(12) United States Patent
Chantasirivisal et al.

(10) Patent No.: US 12,714,863 B2
(45) Date of Patent: Aug. 25, 2026

(54) IMPLANTABLE LEAD HAVING VARIABLE ELECTRODE SPACING

(71) Applicant: Pacesetter, Inc., Sylmar, CA (US)

(72) Inventors: Steve Chantasirivisal, Santa Clarita, CA (US); Keith Victorine, Santa Clarita, CA (US); Wesley Alleman, Santa Clarita, CA (US); Robert Shaw, Castaic, CA (US)

(73) Assignee: Pacesetter, Inc., Sylmar, CA (US)

( * ) Notice: Subject to any disclaimer, the term of this patent is extended or adjusted under 35 U.S.C. 154(b) by 270 days.

(21) Appl. No.: 18/531,530

(22) Filed: Dec. 6, 2023

(65) Prior Publication Data

US 2024/0189601 A1 Jun. 13, 2024

Related U.S. Application Data

(60) Provisional application No. 63/431,455, filed on Dec. 9, 2022.

(51) Int. Cl.

*A61N 1/362* (2006.01)
*A61N 1/05* (2006.01)
*A61N 1/39* (2006.01)

(52) U.S. Cl.

CPC ........... *A61N 1/362* (2013.01); *A61N 1/0573* (2013.01); *A61N 1/3956* (2013.01)

(58) Field of Classification Search

CPC .. A61N 1/0573; A61N 1/059; A61N 1/37518; A61N 1/0575

See application file for complete search history.

(56) References Cited

U.S. PATENT DOCUMENTS

| | | | | |
|---|---|---|---|---|
| 7,027,876 | B2 | 4/2006 | Casavant et al. | |
| 7,245,973 | B2 | 7/2007 | Liu et al. | |
| 7,657,326 | B2 | 2/2010 | Bodner et al. | |
| 8,078,287 | B2 | 12/2011 | Liu et al. | |
| 8,406,899 | B2 | 3/2013 | Reddy et al. | |
| 2007/0299493 | A1* | 12/2007 | Osypka ................ | A61N 1/0573 607/127 |
| 2009/0259272 | A1 | 10/2009 | Reddy et al. | |

FOREIGN PATENT DOCUMENTS

WO 2021083792 A1 5/2021

* cited by examiner

*Primary Examiner* — Alyssa M Alter
(74) *Attorney, Agent, or Firm* — WOMBLE BOND DICKINSON (US) LLP

(57) ABSTRACT

An implantable lead includes an inner lead subassembly contained within and movable relative to an outer lead subassembly. The inner lead subassembly has a helical electrode to pace a target anatomy. The outer lead subassembly includes a ring electrode to sense or pace the target anatomy. A threaded interface interconnects the inner lead subassembly and the outer lead subassembly such that relative rotation of the lead subassemblies causes relative axial movement between the helical electrode and the ring electrode. Other embodiments are also described and claimed.

20 Claims, 7 Drawing Sheets

100
204
202
110
206

110
208
108
206

602
502
504
110

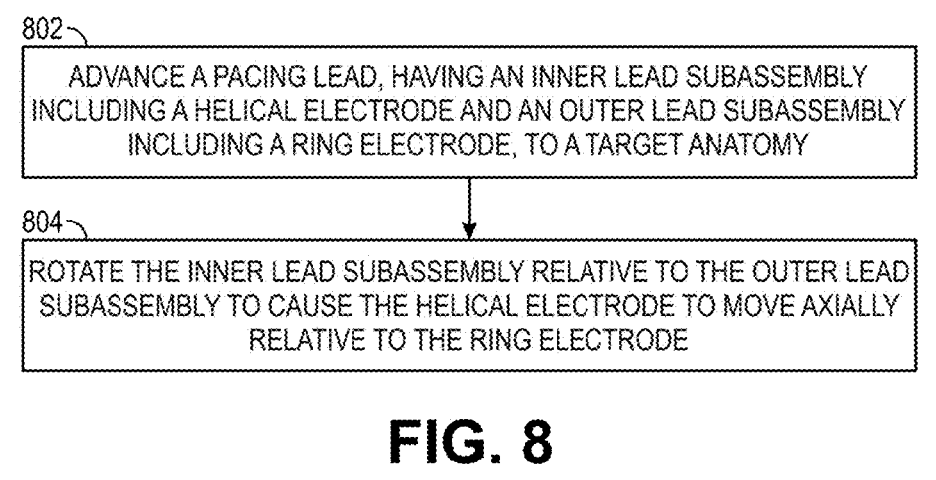

802

ADVANCE A PACING LEAD, HAVING AN INNER LEAD SUBASSEMBLY INCLUDING A HELICAL ELECTRODE AND AN OUTER LEAD SUBASSEMBLY INCLUDING A RING ELECTRODE, TO A TARGET ANATOMY

804

ROTATE THE INNER LEAD SUBASSEMBLY RELATIVE TO THE OUTER LEAD SUBASSEMBLY TO CAUSE THE HELICAL ELECTRODE TO MOVE AXIALLY RELATIVE TO THE RING ELECTRODE

FIG. 8

IMPLANTABLE LEAD HAVING VARIABLE ELECTRODE SPACING

This application claims the benefit of priority of U.S. Provisional Patent Application No. 63/431,455, filed on Dec. 9, 2022, titled "IMPLANTABLE LEAD HAVING VARIABLE ELECTRODE SPACING," which is incorporated herein by reference in its entirety to provide continuity of disclosure.

BACKGROUND

Field

The present disclosure relates to implantable leads and methods of using implantable leads. More specifically, the present disclosure relates to implantable leads useful for septal pacing.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Implantable leads, such as pacing leads, provide an electrical connection between the artificial pacemaker and a target anatomy that is to be electrically stimulated. The target anatomy may be, for example, a His bundle of a heart. Cardiac pacing of the His bundle is clinically effective and advantageous by providing a narrow QRS affecting synchronous contraction of the ventricles. His bundle pacing in or near a membranous septum of a heart, however, has some drawbacks. Successful His bundle pacing cannot always be achieved. Pacing thresholds are often high, sensing is challenging, and success rates can be low.

Pacing at the left bundle branch (LBB) is an alternative to His bundle pacing. Pacing at the LBB involves pacing past the His bundle toward the right ventricle apex. More particularly, a pacing site for LBB pacing is typically below the His bundle, on the interventricular septal wall. To achieve optimal results, the pacing site for physiological pacing at the LBB can be high on the interventricular septal wall, in the region close to the tricuspid valve and pulmonary artery outflow track.

SUMMARY

Existing approaches for left bundle branch (LBB) area pacing use existing pacing leads, which include fixed, invariable spacing between a distal tip of the pacing lead, e.g., a fixed helix of the pacing lead, and an electrode ring. For example, the electrode ring may be spaced 10 mm, or some other predetermined distance, from the fixed helix. To access the LBB, however, the fixed helix is typically driven deeper into a septal wall than the predetermined distance between the fixed helix and the ring electrode. The ring electrode must therefore enter into the septal wall, creating a bore hole and potentially damaging the right bundle branch or other tissue within the septal wall. Furthermore, a position of the ring electrode may not be independently controlled, relative to the positioning of the fixation helix, and the ring electrode may therefore not be optimally positioned for sensing accuracy. Thus, there is a need for an implantable lead having a fixation helix that can extend into the septal wall to engage and pace the LBB, and having a ring electrode that can be independently positioned at an optimal sensing location, such as at a surface of the septal wall.

An implantable lead is described. In an embodiment, the implantable lead includes an inner lead subassembly and an outer lead subassembly. The inner lead subassembly includes a helical electrode mounted on an inner coil extending along a longitudinal axis. The outer lead subassembly includes an outer coil having a central lumen. The outer coil contains the inner coil. More particularly, the inner coil extends through the central lumen. A ring electrode is mounted on the outer coil.

The outer lead subassembly or the inner lead subassembly includes a threaded interface having a threaded surface. For example, the threaded interface can be attached to or integrated with the outer lead subassembly. Alternatively, the threaded interface can be attached to or integrated with the inner lead subassembly. In either case, the threaded surface can be between the outer lead subassembly and the inner lead subassembly. The threaded surface converts rotation of the inner lead subassembly relative to the outer lead subassembly into relative axial movement of the helical electrode relative to the ring electrode. More particularly, rotation of the inner coil relative to the outer coil can cause the helical electrode to extend or retract relative to the ring electrode.

A method of implanting the implantable lead is also described. The method includes advancing the implantable lead to a target anatomy. For example, the ring electrode can be positioned at a surface of a septal wall. The inner lead subassembly is rotated relative to the outer lead subassembly to cause the helical electrode to move axially relative to the ring electrode. The helical electrode can therefore screw into the septal wall to engage tissue at a LBB while the ring electrode remains in place at the surface of the septal wall.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

FIG. 8 is a flowchart of a method of implanting an implantable lead, in accordance with an embodiment.

DETAILED DESCRIPTION

Embodiments describe an implantable lead, e.g., a pacing lead, for cardiac stimulation, e.g., pacing. The implantable lead may, however, be used in other applications, such as deep brain stimulation. Thus, reference to the implantable lead as being used for cardiac, e.g., septal, stimulation is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of an implantable lead. Similarly, "proximal" may indicate a second direction opposite to the first direction. Such terms are provided to establish relative frames of reference, however, and are not intended to limit the use or orientation of an implantable lead to a specific configuration described in the various embodiments below.

In an aspect, an implantable lead includes a helical electrode that is movable relative to a ring electrode. Accordingly, the helical electrode can extend into a septal wall to engage and pace a left bundle branch (LBB), and the ring electrode can be independently positioned at an optimal sensing location, such as at a surface of the septal wall. The variable electrode spacing can allow a user to place both electrodes at their respective optimal implant locations to improve pacing and sensing accuracy.

Figure 1:
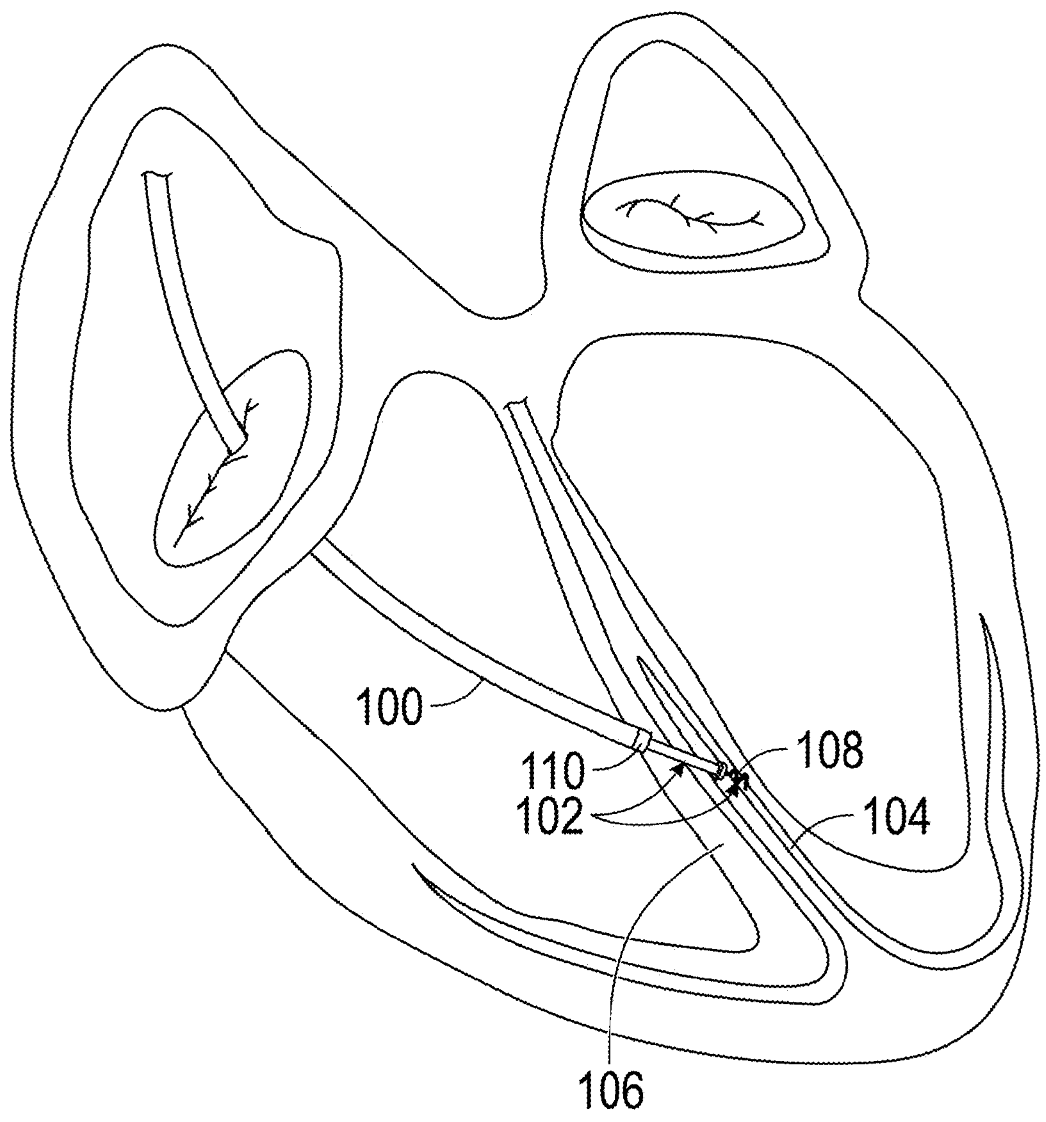
FIG. 1 is a diagrammatic cross-section of a patient heart illustrating an example implantation of an implantable lead in a target anatomy, in accordance with an embodiment.

Referring to FIG. 1, a diagrammatic cross-section of a patient heart illustrating an example implantation of an implantable lead in a target anatomy is shown in accordance with an embodiment. An implantable lead 100, e.g., a pacing lead or an implantable cardioverter defibrillator lead, may be a transvenous lead that can be delivered to a target anatomy 102 to conductively pace the target anatomy. The target anatomy 102 can include a septal wall 106 of a heart and/or a LBB 104 in the septal wall 106.

In an embodiment, the implantable lead 100 can include an active fixation helix, e.g., a helical electrode 108. The helical electrode 108 can be extendable, relative to a ring electrode 110, and driven into the interventricular septum to engage and anchor the implantable lead 100 to the tissue. The helical electrode 108 can be an active electrode, and thus, can pace the tissue. When the helical electrode 108 is located at the LBB 104, the ring electrode 110 can be located at or on a surface of the septal wall 106. The ring electrode 110 can be a passive or an active electrode. Accordingly, the variable spacing of the electrodes can facilitate optimal placement of each electrode to provide a more robust multisite pacing modality.

Figures 2A, 2B:
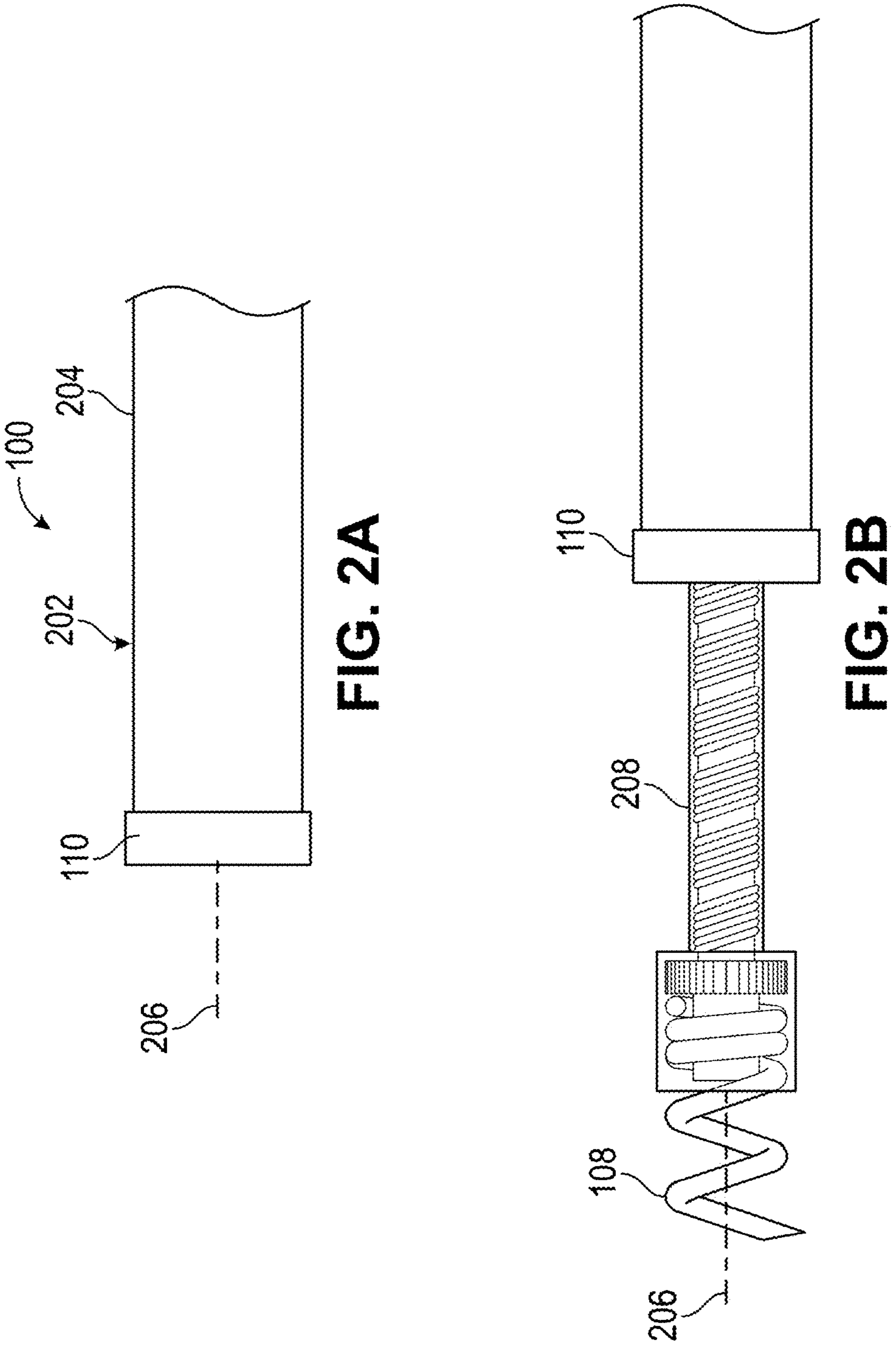
FIGS. 2A-2B are side views of an implantable lead having variable electrode spacing, in accordance with an embodiment.

Referring to FIG. 2A, a side view of an implantable lead having a helical electrode aligned with a ring electrode is shown in accordance with an embodiment. The implantable lead 100 can include an outer lead subassembly 202. The outer lead subassembly 202 can include an elongated outer lead body 204 extending longitudinally along a longitudinal axis 206. More particularly, the longitudinal axis 206 can be a central axis of the implantable lead 100, along which the implantable lead 100 extends. In an embodiment, the outer lead subassembly 202 includes the ring electrode 110 mounted on a distal end of the outer lead body 204. The outer lead body 204 can include a tubular structure, having the components described below. Similarly, the ring electrode 110 can have an annular or tubular structure, and can be mounted on the outer lead body 204 such that a central lumen (FIG. 3) of the outer lead subassembly 204 and a central opening of the ring electrode 110 coincide.

Referring to FIG. 2B, a side view of an implantable lead having a helical electrode spaced apart from a ring electrode by a first distance is shown in accordance with an embodiment. The implantable lead 100 can include an inner lead subassembly 208, positioned within the outer lead subassembly 202. More particularly, the inner lead subassembly 208 can extend along the longitudinal axis 206 through the central lumen of the outer lead body 204. Accordingly, components of the inner lead subassembly 208 can be contained within the central lumen of components of the outer lead subassembly 202, as described below.

Whereas the inner lead subassembly 208 is represented in a retracted state in FIG. 2A, the inner lead subassembly 208 is shown in an extended state in FIG. 2B. More particularly, rather than being longitudinally aligned with each other in the retracted state, as represented in FIG. 2A, the ring electrode 110 and a helical electrode 108 of the inner lead subassembly 208 can be longitudinally spaced apart from each other in the extended state, as shown in FIG. 2B.

Relative movement between the helical electrode 108 and the ring electrode 110 can be caused by movement input to the inner lead subassembly 208. For example, the inner lead subassembly 208 may be pushed, pulled, or rotated to cause relative longitudinal movement between the subassemblies. The longitudinal movement can vary the distance between the electrodes. Furthermore, the variable spacing allows the helical electrode 108 to be driven to an optimal location within the target anatomy 102, e.g., at the LBB 104, while maintaining the ring electrode 110 at a respective optimal location, e.g., on the surface of the septal wall 106. Accordingly, via variable tip-to-ring spacing, the implantable lead 100 allows the pacing helix to extend to any distance to access the conduction system for physiological pacing while keeping the electrode ring at the tissue surface. An architecture of an assembly that converts rotational movement of the inner lead subassembly 208 to relative movement of the electrodes 108, 110, in an embodiment, is described below.

Figure 3:
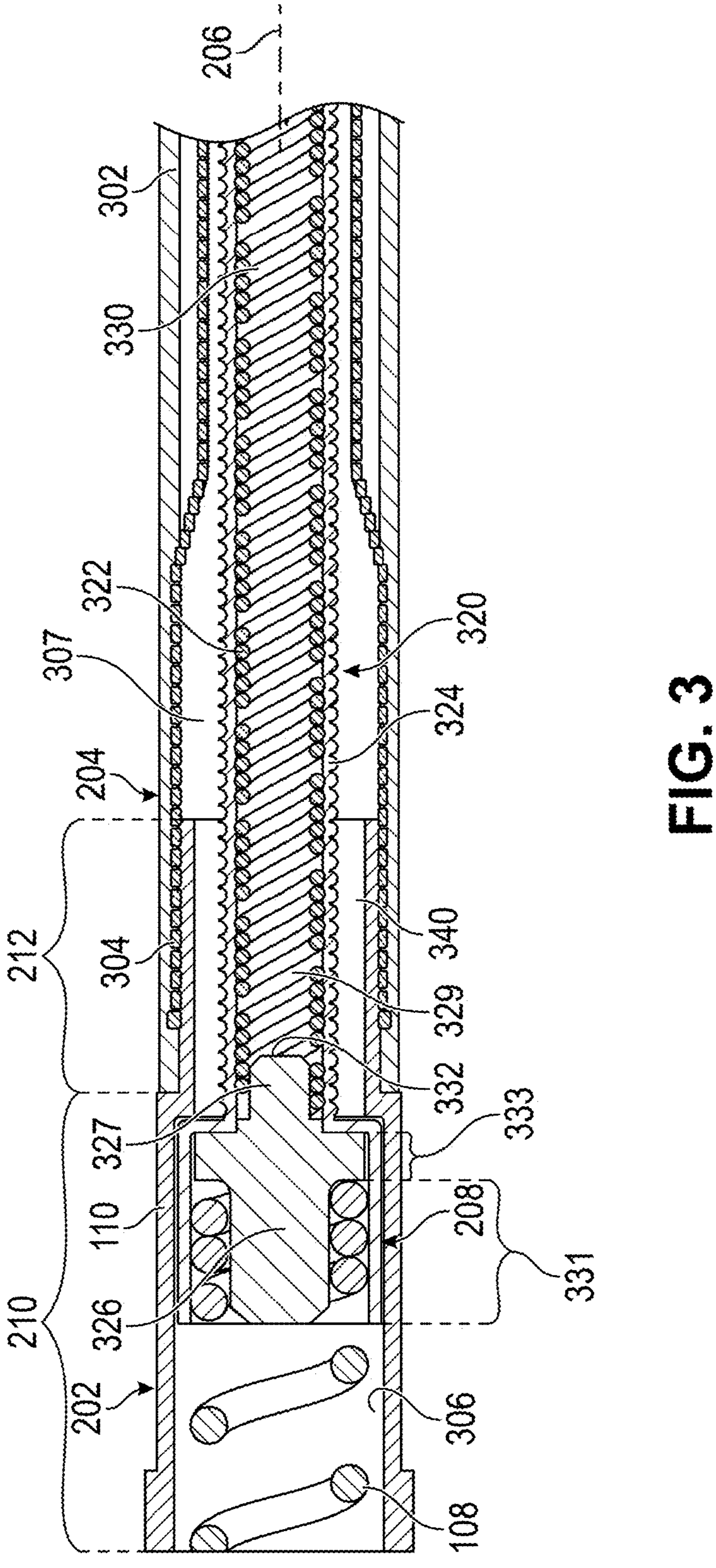
FIG. 3 is a cross-sectional view of an implantable lead, in accordance with an embodiment.

Referring to FIG. 3, a cross-sectional view of an implantable lead is shown in accordance with an embodiment. The outer lead subassembly 202 having the outer lead body 204 can be further divided into individual components. In an embodiment, the outer lead body 204 includes an outer jacket 302 having a tubular, elongate structure. The outer jacket 302 may, for example, be an insulating jacket surrounding an outer coil 304. More particularly, the outer coil 304 can include a coil extending from a proximal region of the implantable lead 100 (not shown) to a distal region of the implantable lead 100 (shown in FIG. 3), and the outer jacket 302 can be a silicone sleeve or layer mounted on the outer coil 304. The outer coil 304 may be formed from an electrically conductive material to conduct sensing or stimulation, e.g., pacing, pulses from an external stimulation, e.g., pacing, device to the ring electrode 110. Accordingly, the outer jacket 302 can insulate the outer coil 304 from a surrounding environment over a length that the outer jacket 302 covers the outer coil 304. In combination, the outer jacket 302 and the outer coil 304 can form the outer lead body 204 having a central lumen 306 through which the inner lead subassembly 208 extends.

The ring electrode 110 can be mounted on the outer coil 304. For example, the ring electrode 110 can have a stepped outer surface, which includes a distal ring portion 210 and a proximal ring portion 212. The distal ring portion 210 may have an outer dimension that is larger than the proximal ring portion 212. In an embodiment, the proximal ring portion 212 can fit within a central channel 307 of the outer coil 304. The central channel 307 can be a portion of the central lumen 306. The outer coil 304 can be attached to the proximal ring portion 212 to secure the components. Accordingly, the ring electrode 110 can be mounted on an interior surface of the outer coil 304, within the central channel 307. The outer jacket 302 may be applied over the outer coil 304 and the proximal ring portion 212 to electrically insulate those components from the surrounding environment. In contrast, the distal ring portion 210 can be exposed to the surrounding environment.

The inner lead subassembly 208 can include an inner lead body 320, which like the outer lead body 204, may have a tubular, elongate structure. The inner lead body 320 can have an inner coil 322 extending helically about, and longitudinally along, the longitudinal axis 206. More particularly, the inner coil 322 can extend along the longitudinal axis 206 within the central lumen 306. The inner coil 322 may be formed from an electrically conductive material, and thus, can conduct electrical stimulation pulses from the external stimulation device to the helical electrode 108.

The outer coil 304 and the inner coil 322 may be separated from each other by an insulative jacket. For example, the inner lead body 320 may include an inner jacket 324 covering the inner coil 322. The inner jacket 324 may be formed from an electrically insulating material such as silicone. The inner jacket 324 may be layered on or slip fit over the inner coil 322. Accordingly, the inner jacket 324 can insulate the inner coil 322 from the interior surface of the outer coil 304, and thus, avoid an electrical short between the coils that could disrupt sensing or stimulation pulses.

The helical electrode 108 can be mounted on the inner coil 322. For example, the helical electrode 108 can be mounted directly on the inner coil 322 and attached thereto. In an embodiment, as shown in FIG. 3, the helical electrode 108 may be indirectly mounted on the inner coil 322. More particularly, the inner coil lead subassembly 320 can include an electrode mount 326 to interconnect the helical electrode 108 and the inner coil 322. The electrode mount 326 can be mounted on the inner coil 322. For example, the electrode mount 326 can have a proximal boss 327 that extends into a central channel 329 of the inner coil 322. The proximal boss 327 can be attached to the inner coil 322 to secure the electrode mount 326 to the inner coil 322.

The electrode mount 326 may also include a distal portion having a distal boss 331 and a mount base 333. The mount base 333 may be distal to the proximal boss, and can have an outer dimension that is larger than an outer dimension of the helical electrode 108. By contrast, the distal boss 331 of the distal portion can have an outer dimension that is less than an inner dimension of the helical electrode 108. Accordingly, the distal boss 331 can be inserted into the interior of the helical electrode 108. More particularly, the helical electrode 108 can be mounted on the electrode mount 326, e.g., by being fit over the distal boss 331 to bottom out on the mount base 333. The helical electrode 108 can be attached to the electrode mount 326 to secure the helical electrode 108 to the electrode mount 326 and the inner coil 322.

A proximal region of the helical electrode 108, such as the region extending around the mount base 333, can be insulated from the surrounding environment. For example, the inner jacket 324 can extend distally around the inner coil 322, the electrode mount 326, and several proximal turns of the helical electrode 108. The inner jacket 324 can therefore electrically insulate the inner lead subassembly 320 electrical connections and subassembly components, other than the distal turns of the helical electrode 108, and can secure the helical electrode 108 to the inner coil 322.

In an embodiment, the implantable lead 100 can accommodate a stylet. The stylet may be inserted through the implantable lead 100 to push the distal region of the implantable lead 100 during delivery to the target anatomy 102. The stylet can therefore aid in reaching the target anatomy 102 and/or burrowing the implantable lead 100 into the target anatomy 102. The inner coil 322 of the implantable lead 100 can include a stylet lumen 330 (in a same space as the central channel 329) to receive the stylet. The stylet lumen 330 can extend along the longitudinal axis 206 from a proximal end of the implantable lead 100 to the electrode mount 326. More particularly, the electrode mount 326 can have a proximal mount face 332, and the stylet lumen 330 can extend along the longitudinal axis 206 to the proximal mount face 332. The stylet, when delivered through the stylet lumen 330, can contact the proximal mount face 332. A user can push the stylet to transmit axial loads to the distal region of the implantable lead 100.

The implantable lead 100 can include a threaded interface 340 to convert rotational movement of the inner lead subassembly 208 relative to the outer lead subassembly 202 into axial movement of the helical electrode 108 relative to the ring electrode 110. The threaded interface 340 may be a component of the outer lead subassembly 202 or the inner lead subassembly 208. More particularly, the threaded interface 340 can be incorporated between the outer lead subassembly 202 and the inner lead subassembly 208, and may have a surface that is fixed to either the outer lead subassembly 202 or the inner lead subassembly 208. Another surface of the threaded interface 340 may be in contact with, but not fixed to, either the outer lead subassembly 202 or the inner lead subassembly 208. The threaded interface 340 may act as a bushing between the subassemblies, having a first surface in contact with and fixed to a first of the subassemblies, and a second surface in contact with and not fixed to a second of the subassemblies.

Figure 4:
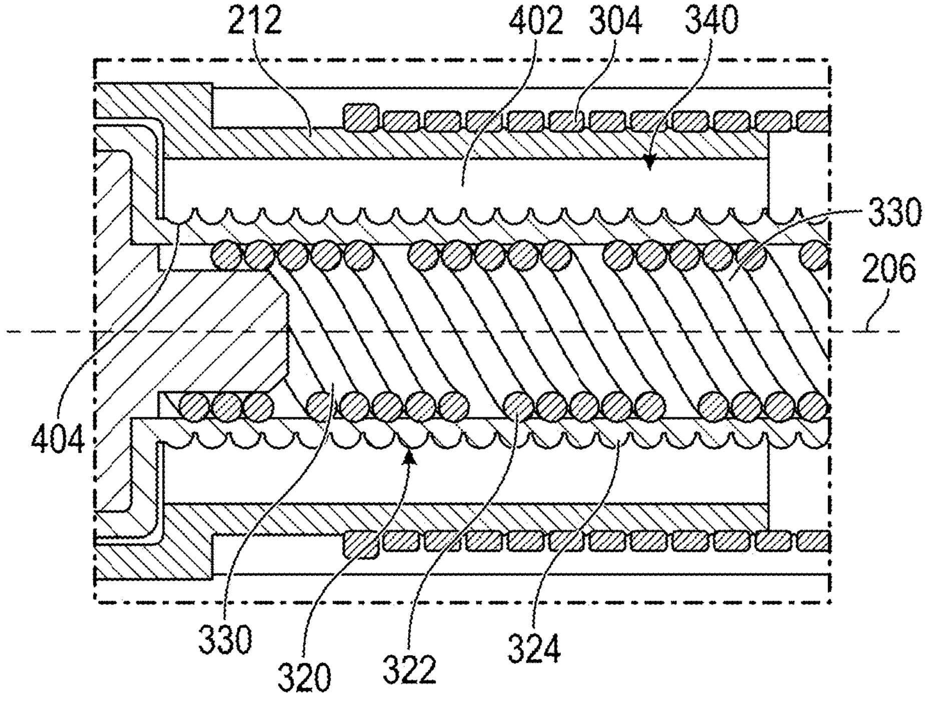
FIG. 4 is a cross-sectional view of a threaded interface of an implantable lead, in accordance with an embodiment.

Referring to FIG. 4, a cross-sectional view of a threaded interface of an implantable lead is shown in accordance with an embodiment. The threaded interface 340 can include a tubular body 402. The tubular body 402 can have an inner surface facing radially inward, e.g., toward the longitudinal axis 206, and an outer surface facing radially outward, e.g., away from the longitudinal axis 206. As shown, the outer surface can be in contact with the proximal ring portion 212 of the ring electrode 110, although it will be appreciated that it may also be in contact with the outer coil 304. Likewise, the inner surface may be in contact with the inner jacket 324 of the inner lead body 320.

In an embodiment, the threaded interface 340 has a threaded surface 404. The threaded surface 404 may be the outer surface and/or the inner surface of the tubular body 402. The threaded surface 404 can be between the outer lead subassembly 202 and the inner lead subassembly 208. More particularly, the threaded surface 404 may be an interface between the outer lead subassembly 202 and the inner lead subassembly 208. For example, the threaded interface 340 may be attached to the outer lead subassembly 202 and the threaded surface 404 can be in contact with the inner lead subassembly 208, as shown in FIG. 4. Alternatively, the threaded interface 340 may be attached to the inner lead subassembly 208 and the threaded surface 404 can be in contact with the outer lead subassembly 202.

The interface can be the surface at which relative movement occurs between the subassemblies. For example, rotation of the inner lead subassembly 208 relative to the outer lead subassembly 202 can cause the inner jacket 324 to rotatably slide along the threaded surface 404 when the tubular body 402 is attached to the outer lead subassembly 202. Similarly, when the tubular body 402 is attached to the inner lead subassembly 208, relative rotation of the subassemblies can cause the outer surface of the tubular body 402, which may be the threaded surface 404 in such case, to slide along the proximal portion of the helical electrode 108 or the outer coil 304. In any case, the threaded surface 404 can convert the relative rotation of the subassemblies into relative axial movement of the subassemblies. Accordingly, the relative rotation of the subassemblies can cause relative axial movement between the helical electrode 108 of the inner lead subassembly 208 relative to the ring electrode 110 of the outer lead subassembly 202.

The threaded surface 404 of the threaded interface 340 may engage a mating, threaded, opposing surface. For example, the outer surface of the inner jacket 324 may be threaded with a thread that matches the thread on the threaded surface 404 of the threaded interface 340. Accordingly, the threaded surfaces can interface to convert rotational movement into translational, longitudinal movement.

In an embodiment, a surface opposed to the threaded surface 404 of the threaded interface 340 is not threaded. The threaded interface 340 may be formed from a material that is harder than a material forming the structure having the opposing surface. For example, the threaded interface 340 may be formed from polyether ether ketone, and the inner jacket 324, which the threaded surface 404 contacts, can be formed from a low durometer silicone material. Accordingly, the threads of the threaded interface 340 can engage and compress the contacting surface of the inner jacket 324. When the threads deform the contacting surface, it forms a threaded coupling between the components. Accordingly, rotation of the threaded interface 340, via rotation of the inner lead subassembly 208, can drive the threaded interface 340 forward along the inner jacket 324 to vary the longitudinal spacing between the electrodes 108, 110.

The threaded interface 340 may be integrally formed with one of the subassemblies. For example, rather than having a tubular body 402 that is attached to the ring electrode 110, the threaded interface 340 may be integrally formed with the ring electrode 110. More particularly, the threaded interface 340 can be a portion of the ring electrode 110 that protrudes into the central lumen 306. The threaded surface 404 can be a thread extending along an interior surface of the ring electrode 110. The thread may be coated with an insulating coating to insulate the helical electrode 108 from the inner lead subassembly 208. For example, the insulating coating can be a parylene coating on the thread. Accordingly, the threaded interface 340 can be more rigid than, and electrically insulated from, an adjacent structure.

In an embodiment, the contacting surface that engages the threaded surface 404 of the threaded interface 340 may have a helical thread corresponding to an underlying coil. The inner coil 322 and the outer coil 304 can be helically wound about the longitudinal axis 206, and thus, can have a helical shape that is constant or variable over a coil length. The respective jacket, e.g., the inner jacket 324 on the inner coil 322, can include a thin sleeve or layer that is loaded onto the underlying coil. The respective jacket may typically be flat. More particularly, the jacket may be a cylindrical tube prior to being loaded onto the coil. The coil, however, may engage and deform the jacket when the jacket is loaded onto the coil, e.g., in a press fit. Accordingly, the jacket can be stretched to take the shape of the underlying coil. More particularly, the jacket may have one or more threads corresponding to the outer surface of the coil.

Figures 5, 6:
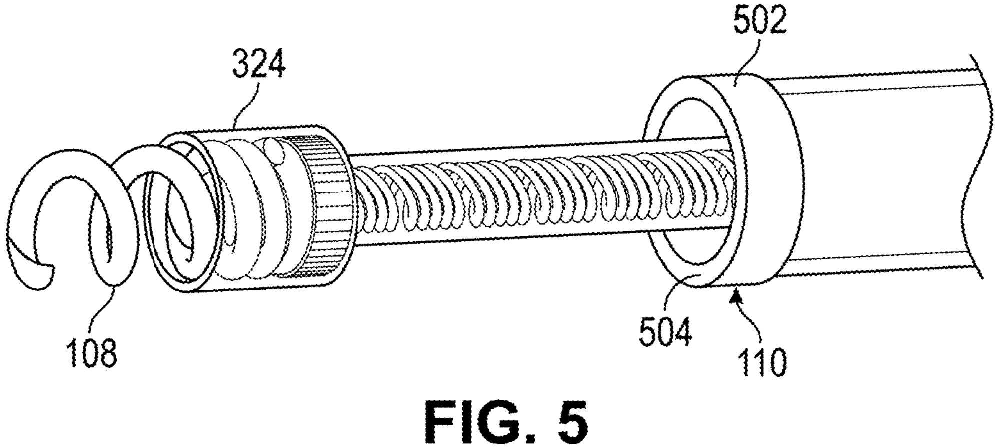
FIG. 5 is a perspective view of an implantable lead having an active ring electrode, in accordance with an embodiment.
FIG. 6 is a perspective view of an implantable lead having a passive ring electrode, in accordance with an embodiment.

Referring to FIG. 5, a perspective view of an implantable lead having an active ring electrode is shown in accordance with an embodiment. The ring electrode 110 can act as an active, pacing electrode. In an embodiment, the ring electrode 110 has an outer ring surface 502 facing radially outward toward the surrounding environment. The outer ring surface 502 can be cylindrical. The ring electrode 110 may also include a distal ring face 504, distal to the outer ring surface 502, facing in a distal direction. When placed against the septal wall 106, the distal ring face 504 can electrically connect the ring electrode 110 to the septal wall tissue. Pacing impulses can be delivered through the electrode-to-tissue contact. For example, the outer coil 304 can deliver pacing impulses from the external pacing device to the ring electrode 110. Thus, the ring electrode 110 can act as an active electrode. Notably, in the extended state, the helical electrode 108 can be distal to and spaced apart from the ring electrode 110. The helical electrode 108 may therefore deliver pacing impulses to tissue within, rather than at the surface, of the septal wall 106. For example, the helical electrode 108 can deliver pacing impulses to the LBB 104. The inner jacket 324 can insulate the implantable lead 100 between the ring electrode 110 and the helical electrode 108 to avoid interference between the pacing delivered from the active electrodes.

Referring to FIG. 6, a perspective view of an implantable lead having a passive ring electrode is shown in accordance with an embodiment. The ring electrode 110 can be partially covered to reduce a likelihood of contact between the ring surface and the septal wall 106. In an embodiment, the distal ring face 504 of the ring electrode 110 is covered by a tip covering 602 (represented with dashed lines to allow visibility of the distal ring face 504). The tip covering 602 may, for example, be a silicone covering that extends over the distal ring face 504 and a portion of the outer ring surface 502. At least a portion of the outer ring surface 502 may remain exposed, however. For example, a proximal region of the outer ring surface 502 can be exposed and face radially outward to contact the surrounding environment, e.g., blood within a ventricle, while the distal ring face 504 is insulated from the septal wall 106. The ring electrode 110 may therefore be a passive electrode used to sense the target anatomy 102. For example, the ring electrode 110 may be used as a reference electrode.

In addition to insulating the distal ring face 504 from the septal wall 106, the tip covering 602 can mechanically buffer the implantable lead 100 against the septal wall 106. More particularly, the tip covering 602 can act like a shock absorber that absorbs pressure applied to the distal end of the implantable lead 100 by pulsating heart tissue. Accordingly, the tip covering 602 can reduce a likelihood of the outer lead subassembly 202 burrowing or migrating further into the septal wall 106 following implantation. The optimal electrode spacing may therefore be retained over time.

Figure 7:
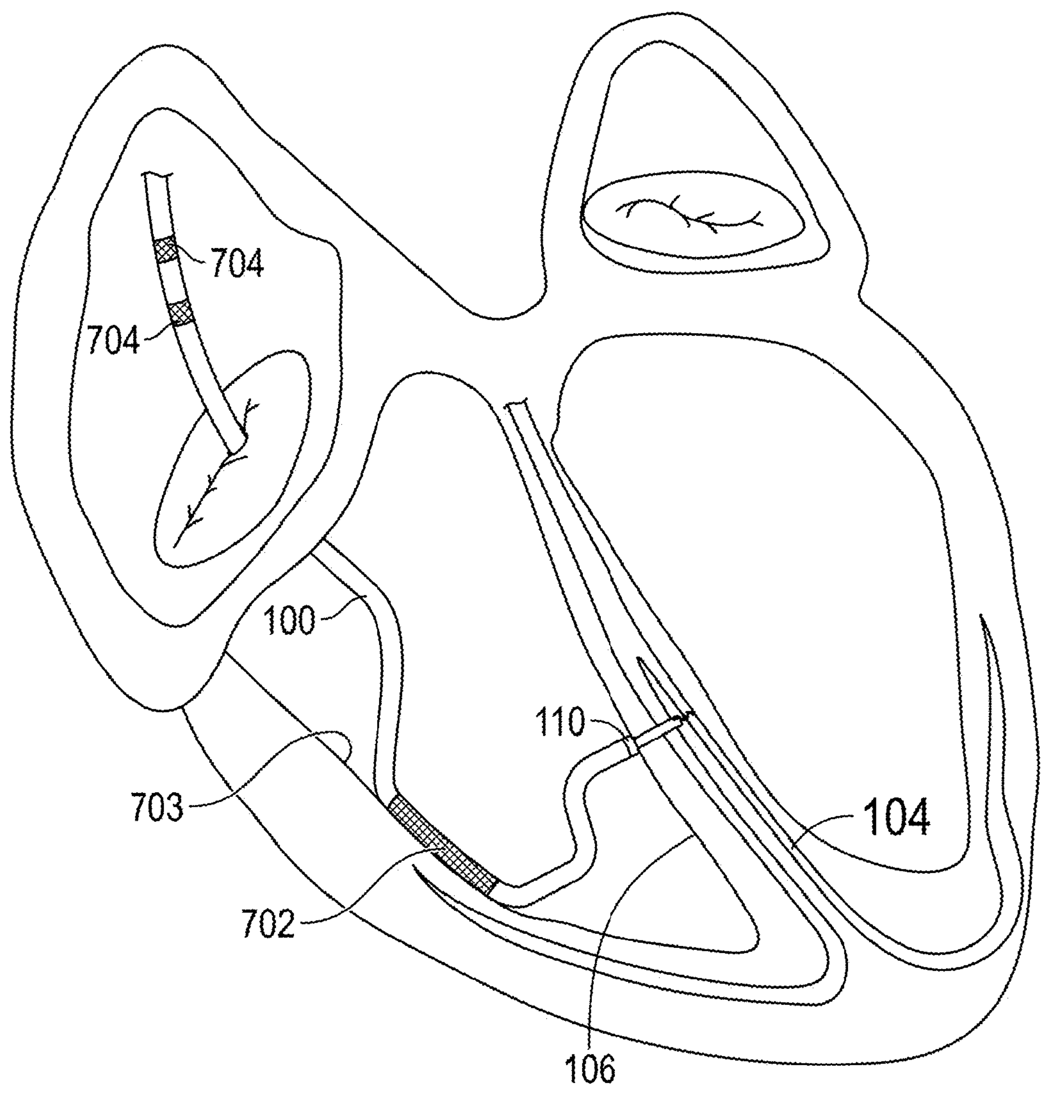
FIG. 7 is a diagrammatic cross-section of a patient heart illustrating an example implantation of an implantable lead in a target anatomy, in accordance with an embodiment.

Referring to FIG. 7, a diagrammatic cross-section of a patient heart illustrating an example implantation of an implantable lead in a target anatomy is shown in accordance with an embodiment. The implantable lead 100 can perform as a defibrillation lead. Accordingly, the implantable lead may can include a shock coil 702. The shock coil 702 can be used to pace the right ventricle in conjunction with the conduction system pacing, and thus, can provide for multi-site stimulation. To that end, the outer lead subassembly 202 can include the shock coil 702 at a location proximal to the ring electrode 110. The shock coil 702 can be sized to apply a defibrillation shock to an appropriate region of the target tissue. For example, the shock coil 702 can have a length in a range of 5 to 10 cm, e.g., 8 cm.

In an embodiment, the shock coil 702 is located such that, when the ring electrode 110 is positioned against the septal wall 106 and the implantable lead 100 curves downward toward a ventricular apex as shown, the shock coil 702 is in contact with an opposite ventricular septal wall 703. The shock coil 702 may, for example, have a distal coil end that is longitudinally spaced from the ring electrode 110 by a distance in a range of 10 to 20 mm, e.g., 15 mm. It will be appreciated that the location may be varied based on the target anatomy 102. For example, when the target anatomy 102 includes the superior vena cava, the shock coil 702 may be spaced appropriately from the ring electrode 110 based on the intended curvature of the implantable lead 100 within the heart when the ring electrode 110 is positioned against the septal wall 106. It will be appreciated that, by having the ring electrode 110 repeatedly positioned at the septal wall surface, rather than burrowing into the septal wall 106, positioning of the shock coil 702 at the intended anatomy can be predictable and consistent.

The implantable lead 100 can include one or more atrial sensing rings 704. An atrial sensing ring 704 can be used for atrial synchronization pacing. In an embodiment, the atrial sensing ring(s) 704 are located such that, when the ring electrode 110 is positioned against the septal wall 106 and the implantable lead 100 curves downward toward a ventricular apex as shown, the atrial sensing ring(s) 704 are positioned within an atrium of the heart. It will be appreciated that, by having the ring electrode 110 repeatedly positioned at the septal wall surface, rather than burrowing into the septal wall 106, positioning of the atrial sensing ring(s) 704 within the atrium can be predictable and consistent.

In addition to improving the repeatability of positioning the shock coil 702 and the atrial sensing ring(s) 704, the ability to maintain the ring electrode 110 at the septal wall surface can also ease the placement of a pre-formed curvature of the implantable lead 100. More particularly, the implantable lead 100 can have a pre-formed curvature to enhance the support of the implantable lead 100 within the target environment. For example, the implantable lead 100 can have a curvature that matches a curvature of the septal wall surrounding the ventricle. By ensuring that the starting point of the curvature, e.g., the ring electrode 110, is repeatably placed at the septal wall 106, it follows that the curvature of the outer lead body 204 will also be repeatably placed along the septal wall 703 curvature.

Referring to FIG. 8, a flowchart of a method of implanting an implantable lead is shown in accordance with an embodiment. At operation 802, the implantable lead 100 can be advanced to the target anatomy 102. The implantable lead 100 may, for example, be delivered through a catheter-based system. To advance the implantable lead 100, a stylet can be inserted into the stylet lumen 330 to lend stiffness to the lead system, and to apply forward pressure to facilitate deep seating of the helical electrode 108 within the septal wall 106. More particularly, a user can push forward on the outer lead subassembly 202 and/or the stylet to drive the implantable lead 100 through a guiding catheter to, and through, the target anatomy 102.

During delivery, the implantable lead 100 may be in the retracted state. More particularly, the inner lead subassembly 208 can be retracted proximally such that the helical electrode 108 is housed within the distal region of the outer lead subassembly 202, e.g., within the central lumen 306 radially inward of the ring electrode 110.

A distalmost surface of the implantable lead 100 in the retracted state, e.g., the distal ring face 504 or the tip covering 602, can be delivered into contact with the septal wall 106. At operation 804, the inner lead subassembly 208 is rotated relative to the outer lead subassembly 202 to cause relative axial movement between the electrodes, and thus, to transition the implantable lead 100 into the extended state. Rotation can be transmitted to the inner coil 322 by a connector pin that is connected to the inner coil 322 at a proximal end of the implantable lead 100. The connector pin can be an electrical connector that engages the external stimulation device during pacing, for example. The rotation of the inner lead subassembly 208 can occur while maintaining the outer lead subassembly 202 in place. Thus, the helical electrode 108 can screw into the septal wall 106 and advance distally while the ring electrode 110 is maintained at the surface of the septal wall 106.

The helical electrode 108 can be driven through the septal wall 106 to an optimal electrode position, e.g., to the LBB 104. A distance between the septal wall 106 and the optimal position may vary. The inner lead subassembly 208 can be rotated as many times as needed to vary the space between the electrodes to match the anatomy. For example, the spacing between the electrodes after implantation can be 2 cm, although alternative depths, deeper or shallower, can be achieved with a corresponding number of relative rotations between the lead coils.

When the electrodes are positioned at the optimal relative positions, the stylet can be removed. In addition to the benefits described above with respect to optimal relative positioning between the lead electrodes, the implantable lead described above can provide a more flexible implantable lead. More particularly, with the stylet removed, the portion of the implantable lead 100 that is embedded within the septal wall 106 (the inner lead subassembly 320) may be more flexible than existing pacing leads. Accordingly, the implantable lead 100 can reduce a likelihood of mechanically stressing the target tissue.

Following removal of the stylet, the implantable lead 100 can be connected to the external stimulation device. The connection may be through the pin connector and/or a proximal electrical connector coupled to the outer coil 304. The connectors can be plugged into the external stimulation device. Accordingly, pacing and/or sensing impulses may be communicated through the implantable lead 100 to or from the helical electrode 108 and/or ring electrode 110 that are variably spaced relative to each other.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. An implantable lead, comprising:

an inner lead subassembly including a helical electrode mounted on an inner coil positioned within an inner jacket, the inner coil and the inner jacket extending along a longitudinal axis; and an outer lead subassembly including an outer coil having a central lumen containing the inner coil, and a ring electrode mounted on the outer coil, wherein the outer lead subassembly includes a threaded interface having a threaded surface between the outer lead subassembly and the inner jacket, and wherein the threaded surface converts rotation of the inner lead subassembly relative to the outer lead subassembly into relative axial movement of the helical electrode relative to the ring electrode.

2. The implantable lead of claim 1, wherein the threaded interface includes a tubular body having the threaded surface.

3. The implantable lead of claim 1, wherein the threaded surface contacts an opposing threaded surface of the inner jacket.

4. The implantable lead of claim 1, wherein a distal ring face of the ring electrode is exposed, and wherein the ring electrode is an active electrode.

5. The implantable lead of claim 1, wherein a distal ring face of the ring electrode is covered by a tip covering, and wherein the ring electrode is a passive electrode.

6. The implantable lead of claim 1, wherein the outer lead subassembly includes a shock coil.

7. The implantable lead of claim 1, wherein the outer lead subassembly includes one or more atrial sensing rings.

8. The implantable lead of claim 1, wherein the inner lead subassembly includes an electrode mount mounted on the inner coil, wherein the helical electrode is mounted on the electrode mount, and wherein the inner coil has a stylet lumen extending along the longitudinal axis to a proximal mount face of the electrode mount.

9. An implantable lead, comprising:

an outer lead subassembly including an outer coil having a central lumen, and a ring electrode mounted on the outer coil; and an inner lead subassembly including an inner coil positioned within an inner jacket, the inner coil and the inner jacket extending along a longitudinal axis within the central lumen, and a helical electrode mounted on the inner coil, wherein the inner lead subassembly includes a threaded interface having a threaded surface between the inner jacket and the outer lead subassembly, and wherein the threaded surface converts rotation of the inner lead subassembly into axial movement of the helical electrode relative to the ring electrode.

10. The implantable lead of claim 9, wherein the threaded interface includes a tubular body having the threaded surface.

11. The implantable lead of claim 10, wherein the threaded interface is coupled to the inner lead subassembly, and wherein the threaded surface contacts the outer lead subassembly.

12. The implantable lead of claim 9, wherein a distal ring face of the ring electrode is exposed, and wherein the ring electrode is an active electrode.

13. The implantable lead of claim 9, wherein a distal ring face of the ring electrode is covered by a tip covering, and wherein the ring electrode is a passive electrode.

14. The implantable lead of claim 9, wherein the outer lead subassembly includes a shock coil.

15. The implantable lead of claim 9, wherein the outer lead subassembly includes an atrial sensing ring.

16. The implantable lead of claim 9, wherein the inner lead subassembly includes an electrode mount mounted on the inner coil, wherein the helical electrode is mounted on the electrode mount, and wherein the inner coil has a stylet lumen extending along the longitudinal axis to a proximal mount face of the electrode mount.

17. A method, comprising:

advancing an implantable lead to a target anatomy, wherein the implantable lead includes an inner lead subassembly including a helical electrode mounted on an inner coil, the inner coil positioned within an inner jacket, an outer lead subassembly including an outer coil having a central lumen containing the inner coil, and a ring electrode mounted on the outer coil, and a threaded interface having a threaded surface between the outer lead subassembly and the inner jacket; and rotating the inner lead subassembly relative to the outer lead subassembly to cause the helical electrode to move axially relative to the ring electrode.

18. The method of claim 17, wherein the threaded interface includes a tubular body having the threaded surface.

19. The method of claim 18, wherein the outer lead subassembly includes the threaded interface, and wherein the threaded surface contacts the inner lead subassembly.

20. The method of claim 18, wherein the inner lead subassembly includes the threaded interface, and wherein the threaded surface contacts the outer lead subassembly.

* * * * *